(12) United States Patent
Gisler

(10) Patent No.: US 12,292,434 B2
(45) Date of Patent: May 6, 2025

(54) ELASTOMERIC SENSOR COMPONENT WITH AN INTEGRATED SENSOR MODULE

(71) Applicant: Dätwyler Schweiz AG, Schattdorf (CH)

(72) Inventor: Sven Gisler, Schattdorf (CH)

(73) Assignee: Dätwyler Schweiz AG, Schattdorf (CH)

( * ) Notice: Subject to any disclaimer, the term of this patent is extended or adjusted under 35 U.S.C. 154(b) by 356 days.

(21) Appl. No.: 18/014,809

(22) PCT Filed: Jun. 30, 2021

(86) PCT No.: PCT/CH2021/050012
§ 371 (c)(1),
(2) Date: Jan. 6, 2023

(87) PCT Pub. No.: WO2022/006686
PCT Pub. Date: Jan. 13, 2022

(65) Prior Publication Data
US 2023/0333082 A1 Oct. 19, 2023

(30) Foreign Application Priority Data
Jul. 7, 2020 (CH) .................................. 00835/20

(51) Int. Cl.
*G01N 33/44* (2006.01)
*H01Q 1/22* (2006.01)
(Continued)

(52) U.S. Cl.
CPC ......... *G01N 33/442* (2013.01); *H01Q 1/2216* (2013.01); *H01Q 7/00* (2013.01);
(Continued)

(58) Field of Classification Search
CPC ...... G01N 33/442; H01Q 1/2216; H01Q 7/00; B29C 43/18; B29C 2043/182;
(Continued)

(56) References Cited

U.S. PATENT DOCUMENTS

| 6,806,808 | B1 | 10/2004 | Watters |
| 9,237,211 | B2 * | 1/2016 | Tabe ..................... H04W 52/04 |
| 9,554,465 | B1 | 1/2017 | Liu |
| 10,165,689 | B1 | 12/2018 | Atwood |

(Continued)

FOREIGN PATENT DOCUMENTS

| CA | 2797810 | 11/2011 |
| DE | 10 2008 006390 A1 | 7/2009 |

(Continued)

OTHER PUBLICATIONS

Office Action dated Jul. 15, 2024 for U.S. Appl. No. 18/014,844.
(Continued)

*Primary Examiner* — Suman K Nath
(74) *Attorney, Agent, or Firm* — Paul D. Bianco; Fleit Intellectual Property Law

(57) ABSTRACT

An elastomeric sensor component includes a component body made of elastomer material and a sensor module embedded within the component body. The sensor module includes a sensor chip, a radiofrequency transponder chip electrically connected to the sensor chip, and a loop antenna electrically connected to the radiofrequency transponder chip. The elastomeric sensor component further includes a booster antenna having a booster antenna loop, with the booster antenna loop deposited on a surface of the component body in order to allow near field data communication and energy transfer with the loop antenna.

17 Claims, 2 Drawing Sheets

(51) Int. Cl.
*H01Q 7/00* (2006.01)
*B29C 43/18* (2006.01)
*B29K 21/00* (2006.01)
*B29L 31/34* (2006.01)

(52) U.S. Cl.
CPC ........ *B29C 43/18* (2013.01); *B29C 2043/182* (2013.01); *B29K 2021/00* (2013.01); *B29L 2031/3456* (2013.01)

(58) Field of Classification Search
CPC ........ B29K 2021/00; B29L 2031/3456; G06K 19/0716; G06K 19/07794
See application file for complete search history.

(56) References Cited

U.S. PATENT DOCUMENTS

| | | |
|---|---|---|
| 10,233,870 B2 | 3/2019 | Gisler |
| 10,830,184 B2 | 11/2020 | Haberland |
| 2008/0061945 A1 | 3/2008 | Hoshina |
| 2011/0094676 A1 | 4/2011 | Husemann |
| 2015/0033823 A1 | 2/2015 | Blumberg |
| 2016/0091544 A1 | 3/2016 | Daneshmand |
| 2016/0192474 A1 | 6/2016 | Niskala |
| 2017/0211514 A1 | 7/2017 | Gisler |
| 2017/0284968 A1 | 10/2017 | Blumberg |
| 2017/0292920 A1 | 10/2017 | Torun |
| 2018/0042479 A1 | 2/2018 | Yalcinkaya |
| 2018/0174015 A1 | 6/2018 | Destraves |
| 2018/0192874 A1 | 7/2018 | Koele et al. |
| 2018/0284034 A1 | 10/2018 | Torum |
| 2018/0328314 A1 | 11/2018 | Haberland |
| 2019/0298234 A1 | 10/2019 | Omenetto |
| 2020/0108672 A1 | 4/2020 | Hosomi |
| 2023/0273140 A1 | 8/2023 | Gisler |
| 2023/0300988 A1 | 9/2023 | Vrijens |
| 2023/0309985 A1* | 10/2023 | Szivek ............... G01L 1/26 606/232 |

FOREIGN PATENT DOCUMENTS

| | | |
|---|---|---|
| EP | 1522957 A1 | 4/2005 |
| EP | 3 578 395 A1 | 12/2019 |
| EP | 3632666 A1 | 4/2020 |
| JP | 2003-16412 A | 1/2003 |
| JP | 2015-228533 A | 12/2015 |
| JP | 2016-114541 A | 6/2016 |
| WO | 2009/120231 A1 | 10/2009 |
| WO | 2013/188443 A2 | 12/2013 |
| WO | 2016/012233 A1 | 1/2016 |
| WO | 2017/121668 A1 | 7/2017 |
| WO | 2018/226782 A1 | 12/2018 |
| WO | 2019/036812 A1 | 2/2019 |
| WO | 2019/173264 A1 | 9/2019 |
| WO | 2020/040709 A1 | 2/2020 |

OTHER PUBLICATIONS

Salim, Complementary Split-Ring Resonator-Loaded Microfluidic Ethanol Chemical Sensor, Sensors, 2016, 13 pages.
International Preliminary Report on Patentability with Written Opinion for PCT/CH2021/050012, filed Jun. 30, 2021.
International Preliminary Report on Patentability with Written Opinion for PCT/CH2021/050013, filed Jun. 30, 2021.
International Preliminary Report on Patentability with Written Opinion for PCT/CH2021/050014, filed Jun. 30, 2021.
Restriction Requirement dated Aug. 30, 2024 for U.S. Appl. No. 18/014,831.
International Search Report and Written Opinion for PCT/CH2021/050013, filed Jun. 30, 2021.
International Search Report and Written Opinion for PCT/CH2021/050012, filed Jun. 30, 2021.
International Search Report and Written Opinion for PCT/CH2021/050014, filed Jun. 30, 2021.

* cited by examiner

ELASTOMERIC SENSOR COMPONENT WITH AN INTEGRATED SENSOR MODULE

TECHNICAL FIELD

The invention relates to an elastomeric sensor component with an integrated sensor module embedded within a component body of elastomer material. It further relates to a sensor system including the elastomeric sensor component and a process for manufacturing an elastomeric sensor component.

BACKGROUND

US2018174015 and EP3578395 describe an electronic component comprising a radiofrequency transponder (RFID) including an electronic chip equipped with a primary antenna connected electrically to the electronic chip and a radiating antenna communicating with a radiofrequency reader. The primary antenna is electromagnetically coupled to the radiating antenna, which may be a single-strand helical spring forming an electric dipole. The electronic component including the radiating antenna is entirely embedded in rubber, e.g. a tire. EP3632666 describes a similar device entirely embedded in rubber. The device may include a sensor. The manufacturing of these known devices is elaborate and prone to manufacturing defect because of the comparatively large size and the fine structure of the radiating antenna. Generally speaking, the larger the embedded part, the more difficult it is to achieve good bonding to the surrounding elastomer material.

WO18226782 describes an electronic device entirely embedded in a small article made of elastomer material. The device may comprise a sensor and a RFID element enabling communication with a corresponding reading device in a wireless way. The electronic device does however not have secondary radiating or booster antenna, leading to only limited reading range.

SUMMARY OF THE INVENTION

It is an objective of the invention to provide a elastomeric sensor component with an component body made of elastomer material including a sensor module embedded within the component body, which is able to detect parameters within the elastomer material and communicate these to an external device. It is a further objective to provide such component, which is cost-efficient in manufacturing and less prone to manufacturing defects, e.g. inclusion of bubbles in the elastomer material.

At least one of the objectives of the present invention is achieved by an elastomeric sensor component according to claim 1 and a sensor system according to claim 8. The elastomeric sensor component comprises a component body made of elastomer material and a sensor module embedded within the component body. The sensor module comprises a sensor chip, a radiofrequency transponder chip electrically connected to the sensor chip, and a loop antenna electrically connected to the radiofrequency transponder chip. The elastomeric sensor component further comprises a booster antenna comprising a booster antenna loop, wherein the booster antenna loop is deposited (e.g. by printing) on a surface of the component body in order to allow near field data communication and energy transfer with the loop antenna. Accordingly, the part, i.e. the sensor module, to be embedded in the component body can be designed very small with a simple shape, e.g. with size and shape as small or even smaller as a one Euro cent coin. Such a sensor module design can withstand the high temperatures and pressures during the vulcanization process of the elastomer material. After vulcanization, the more fragile booster antenna is deposited on the component body. Preferably, the sensor module is entirely embedded in the component body. On the other hand, a part of the sensor module, e.g. a sensing part of the sensor chip, may surface and is thereby not covered by the elastomer material.

The booster antenna loop is preferably concentrically aligned with the loop antenna of the sensor module at a predefined distance.

The shape and size of the loop antenna and the booster antenna loop are designed to achieve optimal data and energy transfer, while being as small as possible. The loops are preferably of circular shape. The booster antenna loop may have the same or a larger diameter than the loop antenna. The space between the loops may be in the range of a 1 to 5 mm.

Further embodiments of the invention are set forth in the dependent claims.

In some embodiments the booster antenna may comprise two booster antenna arms. The booster antenna arms may be of straight or meander-like shape and/or the booster antenna arms and the booster antenna loop are arranged in a plane. It is also possible that the booster antenna arms are at an angle to the plane of the booster antenna loop.

In some embodiments the booster antenna arms may be deposited together with the booster antenna loop on the surface of the component body. Alternatively, the booster antenna arms may project at least partly away from the elastomeric body and may be deposited on or formed by a part different to the elastomeric body.

In some embodiments the booster antenna may be deposited on the surface by printing, e.g. using known printing technologies such as screen printing, flexographic printing, gravure printing, relief printing, inkjet printing, piezo-inkjet printing, aerosol jet printing, stencil printing, offset printing, doctor blade printing, rotary screen printing, intaglio printing, digital printing, capillary printing, electrohydrodynamic printing, tampography. microcontact printing, laser printing; coating or lamination technologies.

In some embodiments the booster antenna deposited on the surface of the component body may be covered with a dielectric layer, e.g. a dielectric foil or a dielectric ink or lacquer, different to the material of the component body. Dielectric inks are typically composed of organic polymers or ceramics in solvents. Novel insulating 2D nanomaterials such as hexagonal boron nitride further offer temperature and electrochemical stability. Dielectric foils may be composed of organic polymers and may include ceramic powder. Good results have been achieved with dielectric ink based on a siloxane polymer composition filled with aluminium oxide resulting in a semi-transparent and stretchable film.

In some embodiments the material for the booster antenna may be selected from the group of conductive polymers, carbon, organic/metallic compounds, metal precursors, and metal nanopowders. Preferably, the material of the booster antenna is a stretchable material, e.g. a stretchable silver ink. The material may be selected from metal inks and/or metal-salt inks, such as Ag/AgCl, Cu and Ni, non-metal inks, e.g. carbon based inks (graphene, carbon nano tube), PEDOT:PSS and combinations thereof. The material may be combined with stretchable carrier materials such as polysiloxane or PU or fluoroelastomer. Good results have been achieved with a silver-siloxane polymer composition.

In some embodiments the elastomer material of the component body may be a thermoset elastomer or a thermoplastic elastomer (TPE). The elastomer material can be, for example, a synthetic or natural rubber, such as butyl rubber, isoprene rubber, butadiene rubber, halogenated butyl rubber (e.g., bromobutyl rubber), ethylene propylene terpolymer, silicone rubber, fluoro-or perfluoroelastomers, chlorosulfonate, polybutadiene, butyl, neoprene, nitrile, polyisoprene, buna-N, copolymer rubbers such as ethylene-propylene (EPR), ethylene-propylene-diene monomer (EPDM), acrylonitrile-butadiene (NBR or HNBR) and styrene-butadiene (SBR), blends such as ethylene or propylene-EPDM, EPR, or NBR, combinations thereof. The term "synthetic rubbers" also should be understood to encompass materials which alternatively may be classified broadly as thermoplastic or thermosetting elastomers such as polyurethanes, silicones, fluorosilicones, styrene-isoprene-styrene (SIS), and styrene-butadiene-styrene (SBS), as well as other polymers which exhibit rubber-like properties such as plasticized nylons, polyolefins, polyesters, ethylene vinyl acetates, fluoropolymers, and polyvinyl chloride.

In some embodiments the elastomeric sensor component may comprise an insert part different to the sensor module, which is at least partially embedded within the component body. Such an insert part may be a rod or peg of a pump diaphragm or a valve membrane, or a plunger of a syringe. If an insert part protrudes out of the component body, the booster arms may be at least partially deposited on or formed by the insert part.

The invention further relates to a sensor system comprising an elastomeric sensor component as described above and a radiofrequency (RFID) reader device equipped with a communication module for providing energy to the sensor module of the elastomeric sensor component via the booster antenna and reading data from the sensor module via the booster antenna. The sensed data can be read out wirelessly from outside of the elastomer component.

The invention further relates to a process for manufacturing an elastomeric sensor component as described above, comprising the steps of: (a) embedding the sensor module in a component body of elastomer material using a molding technique such as compression molding (CM), injection molding (IM), transfer molding (TM), injection transfer molding (ITM) or injection compression molding (ICM); (b) depositing the booster antenna on the surface of the component body in alignment with the loop antenna of the sensor module.

In some embodiments of the process, the sensor module may be embedded by placing the sensor module between two layers of elastomer material and compression molding the component body with the embedded sensor module.

The surface of the sensor module may be modified to obtain better bonding between module and elastomer body. Preferably the sensor module is coated or covered with a bonding agent before step a) or modified by plasma or corona treatment.

The booster antenna may be protected with a dielectric layer of different material than the component body. Before depositing the booster antenna, the surface of the component body may be modified to increase adhesion of the booster antenna to the component body, preferably by coating with a bonding agent or by plasma or corona treatment.

The elastomeric sensor component may be applied in fields such as predictive maintenance of elastomer components, live monitoring of sensitive elastomer parts, failure detection of elastomer parts, or characterization for design iterations.

BRIEF DESCRIPTION OF THE DRAWINGS

The invention is described in greater detail below with reference to embodiments that are illustrated in the figures. The figures show.

EMBODIMENTS OF THE INVENTION

Figure 1:
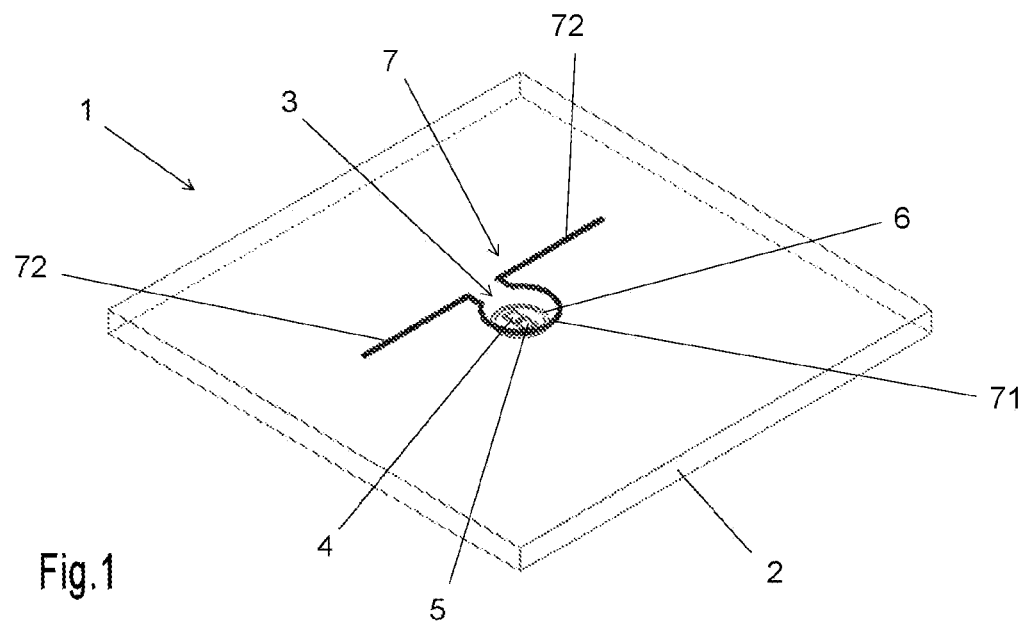
FIG. 1 a perspective view of an elastomeric sensor component.
Figure 2:
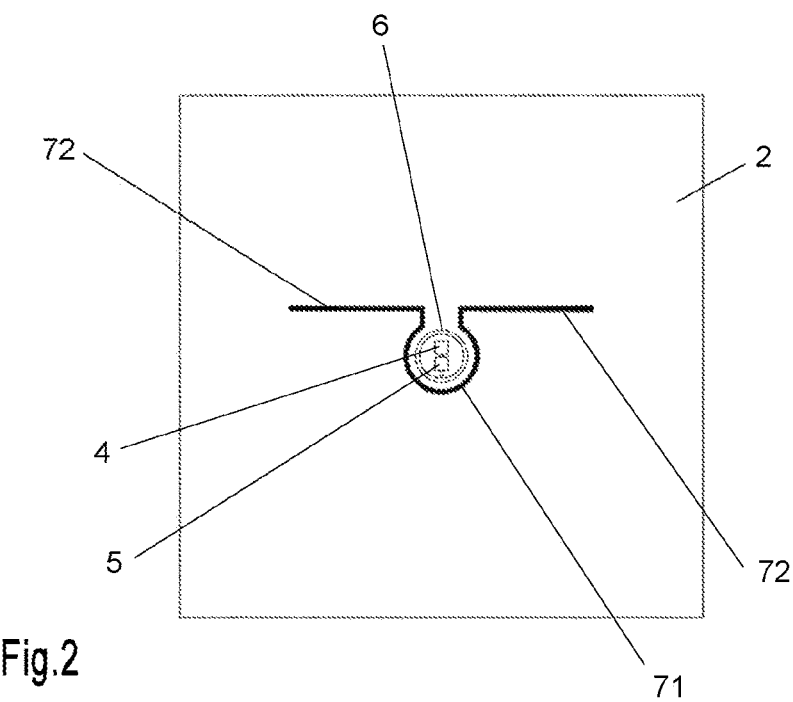
FIG. 2 a top view of the elastomeric sensor component of FIG. 1.
Figure 3:
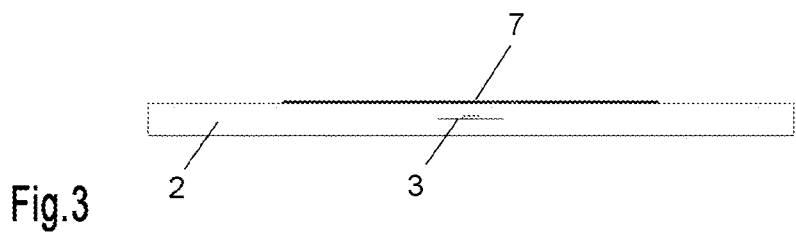
FIG. 3 a side view of the elastomeric sensor component of FIG. 1.

FIG. 1 shows a perspective view of an elastomeric sensor component 1 comprising a component body 2 of elastomer material, a sensor module 3 and a booster antenna 7. In the example shown, the sensor module 3 is entirely embedded in the component body 2. Alternatively, a part of the sensor module, e.g. a sensing part of the sensor chip, may surface and is thereby not covered by the elastomer material. The component body 2 is shown transparent to see the sensor module 3. FIG. 2 shows a top view of the elastomeric sensor component of FIG. 1 and FIG. 3 shows a side view of the elastomeric sensor component of FIG. 1.

The sensor module 3 comprises a sensor chip 4, e.g. a temperature sensor, a radiofrequency transponder chip 5 (RFID chip) including an interface to electrically connect the sensor chip 4 to the RFID chip 5, and a loop antenna 6 electrically connected to the RFID chip 5. These components may be placed on a coin-shaped circuit board of a few millimetres in diameter, with the loop antenna 6 surrounding the two chips 4, 5.

The entire sensor module 3 is embedded in the component body 2 made of elastomer material. The elastomer material may be selected from the group of a thermoset elastomer or a thermoplastic elastomer. Good results have been achieved with ethylene propylene diene monomer rubber (EPDM).

A booster antenna 7 comprising a booster antenna loop 71 and two booster antenna arms 72 is deposited on the surface of the component body 2 in a way that the booster antenna loop 71 is concentrically aligned with the antenna loop 6 of the sensor module 3. The booster antenna 7 as shown in FIGS. 1 and 2 has straight shaped booster antenna arms 72. The printed booster antenna 7 has a unique shape which ensures the inductive coupling between the loop antenna 6 of the sensor module 3 and the booster antenna 7. Good results have been achieved with printing the booster antenna 7 with a stretchable ink or paste, e.g. a stretchable silver ink, to ensure the stretchable properties of the elastomer material. Preferably, the surface is treated by plasma to ensure a good adhesion.

Figure 4:
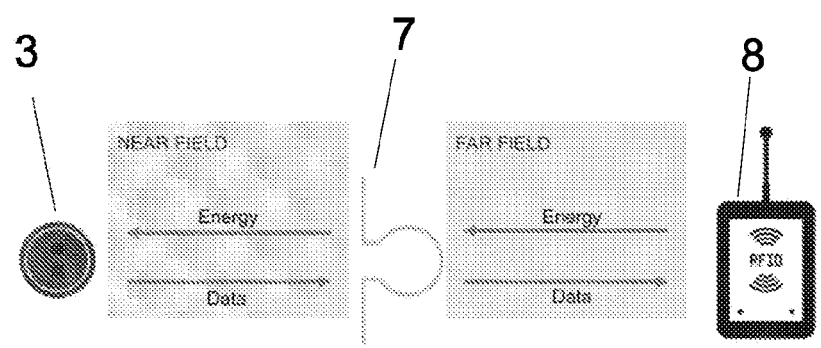
FIG. 4 a diagram of a sensor system using the component of FIG. 1.

The RFID chip 5 and the loop antenna 6 together with the booster antenna 7 ensure energy supply for the sensor chip 4 and communication of the sensed data via the booster antenna 7 to a radiofrequency reader device (RFID reader) 8 (see FIG. 4).

FIG. 4 shows a diagram of a sensor system comprising an elastomeric sensor component 1 and a radiofrequency (RFID) reader device 8 equipped with a communication module for providing energy to the sensor module 3 of the elastomeric sensor component 1 via the booster antenna 7 and reading data from the sensor module 3 via the booster antenna 7.

REFERENCE SIGNS 1 elastomeric sensor component
2 component body
3 sensor module
4 sensor chip
5 radiofrequency transponder chip
6 loop antenna
7 booster antenna
71 booster antenna loop
72 booster antenna arm
8 radiofrequency (RFID) reader device

The invention claimed is:

1. An elastomeric sensor component comprising a component body made of elastomer material and a sensor module embedded within the component body, the sensor module comprising a sensor chip, a radiofrequency transponder chip electrically connected to the sensor chip, and a loop antenna electrically connected to the radiofrequency transponder chip, wherein the elastomeric sensor component further comprises a booster antenna comprising a booster antenna loop, wherein the booster antenna loop is deposited on a surface of the component body in order to allow near field data communication and energy transfer with the loop antenna.

2. The elastomeric sensor component according to claim 1, wherein the booster antenna comprises two booster antenna arms.

3. The elastomeric sensor component according to claim 2, wherein the booster antenna arms are of straight or meander-like shape and/or the booster antenna arms and the booster antenna loop are arranged in a plane.

4. The elastomeric sensor component according to claim 2, wherein the booster antenna arms are deposited together with the booster antenna loop on the surface of the component body.

5. The elastomeric sensor component according to claim 1, wherein the booster antenna is deposited by printing, coating or lamination technologies.

6. The elastomeric sensor component according to claim 1, wherein the booster antenna deposited on the surface of the component body is covered with a dielectric layer, a dielectric foil or a dielectric ink or lacquer different from the material of the component body.

7. The elastomeric sensor component according to claim 1, wherein the material of the booster antenna is a stretchable material.

8. The elastomeric sensor component according to claim 1, wherein the elastomer material of the component body is a thermoset elastomer or a thermoplastic elastomer.

9. A sensor system comprising the elastomeric sensor component according to claim 1 and a radiofrequency (RFID) reader device equipped with a communication module for providing energy to the sensor module of the elastomeric sensor component via the booster antenna and reading data from the sensor module via the booster antenna.

10. A method for manufacturing the elastomeric sensor component according to claim 1, the method comprising:
embedding the sensor module in a component body of elastomer material using a molding technique
depositing the booster antenna on the surface of the component body in alignment with the loop antenna of the sensor module.

11. The method according to claim 10, wherein the sensor module is embedded by placing the sensor module between two layers of elastomer material and compression molding the component body with the embedded sensor module.

12. The method according to claim 10, wherein a surface of the sensor module is modified to obtain better bonding between the sensor module and the elastomer body before embedding the sensor module.

13. The method according to claim 12, wherein the surface of the sensor module is modified by coating with a bonding agent or by plasma or corona treatment.

14. The method according to claim 10, wherein the booster antenna is protected with a dielectric layer of a different material than the component body.

15. The method according to claim 10, wherein before depositing the booster antenna, the surface of the component body is modified to increase adhesion of the booster antenna.

16. The method according to claim 15, wherein the surface of the component body is modified by coating with a bonding agent or by plasma or corona treatment.

17. The method according to claim 10, wherein the molding technique is compression molding (CM), injection molding (IM), transfer molding (TM), injection transfer molding (ITM) or injection compression molding (ICM).

* * * * *